United States Patent [19]

Guziec, Jr.

[11] 4,438,269

[45] Mar. 20, 1984

[54] 4-DIMETHYLAMINOPYRIDINIUM CHLOROCHROMATE

[75] Inventor: Frank S. Guziec, Jr., Las Cruces, N. Mex.

[73] Assignee: Thiokol Corporation, Chicago, Ill.

[21] Appl. No.: 406,585

[22] Filed: Aug. 9, 1982

[51] Int. Cl.$^3$ .......................... C07F 11/00; C07B 3/00; C07D 333/22; C07D 309/12
[52] U.S. Cl. .......................................... 546/9; 549/70; 549/420; 549/436; 568/322; 568/363; 568/424; 568/426; 568/445; 568/446; 568/485
[58] Field of Search ............................................ 546/9

[56] References Cited

U.S. PATENT DOCUMENTS 4,399,281  8/1983  Guziec .................................. 546/9

OTHER PUBLICATIONS

Sommer et al., Chem. Ab., 89, 122139K, (1978).
Corey et al., Tetrahedron Letters 1975, p. 2647.

*Primary Examiner*—Mark L. Berch
*Attorney, Agent, or Firm*—Gerald K. White; Richard J. Sheridan

[57] ABSTRACT

The novel compound 4-dimethylaminopyridinium chlorochromate has been found to be an effective oxidizing agent for converting alcohols to their respective aldehydes or ketones, especially for the selective conversion of allylic and benzylic alchols to their corresponding aldehydes and ketones.

1 Claim, No Drawings

4-DIMETHYLAMINOPYRIDINIUM CHLOROCHROMATE

BACKGROUND OF THE INVENTION

Chromium (VI) reagents have been widely used in organic chemistry for the oxidation of primary and secondary alcohols to carbonyl compounds. Pyridine-chromium trioxide complexes, pyridinium chlorochromate and bipyridine-chromium trioxide complexes have been especially useful reagents for the mild oxidation of primary alcohols to aldehydes. There are, however, some significant difficulties associated with these reagents. For instance, chromium containing by-products often contaminate the desired products, requiring time-consuming purifications. Also, polymeric, chromium containing tars may be formed which contaminate both the reaction and work-up apparatus. In addition, to date, little useful selectivity has been observed in the oxidation of polyhydroxy compounds using chromium (VI) oxidizing reagants.

SUMMARY OF THE INVENTION

A novel compound, 4-dimethylaminopyridinium chlorochromate, has been discovered which is useful as an oxdizing agent. The compound is especially useful as an oxidizing agent for the conversion of alcohols to their corresponding carbonyl compounds. Furthermore, the compound is a particularly useful oxidizing agent in that it will selectively oxidize allylic and/or benzylic alcohols to their corresponding carbonyls while leaving other alcohol groups which may be present during the oxidation reaction substantially intact. The compound is also useful for selectively oxidizing polyhydroxy compounds when it is desired that only certain selected hydroxyl groups be converted to carbonyls. Thus, for example, steroid compounds containing both hindered secondary hydroxyls and non-hindered secondary hydroxyls may be oxidized with DMAP.HCrO$_3$Cl to convert the hindered secondary hydroxyl group to a ketone, while leaving the non-hindered secondary hydroxyl group substantially intact.

Thus, in accordance with this invention there is provided the compound 4-dimethylaminopyridinium chlorochromate.

In accordance with this invention there is also provided a process for oxidizing an alcohol to a corresponding carbonyl compound by reacting the alcohol and 4-dimethylaminopyridinium chlorochromate.

DETAILED DESCRIPTION OF THE PREFERRED EMBODIMENTS

The compound of this invention, 4-dimethylaminopyridinium chlorochromate, has the following structure:

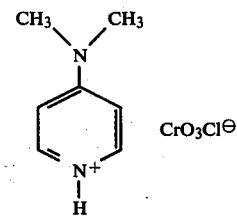

and, for convenience, will sometimes be referred to herein as DMAP.HCrO$_3$Cl.

DMAP.HCrO$_3$Cl may be readily prepared by adding 4-dimethylaminopyridine to a vigorously stirred cold solution of CrO$_3$ in hydrochloric acid. The resulting product is a yellow-orange crystalline solid which is non-hygroscopic and shelf-stable.

DMAP.HCrO$_3$Cl is useful as an oxidizing agent, especially for the selective conversion of alcohols to their corresponding carbonyl compounds. Thus, in the practice of the process of this invention, an alcohol may be converted to the corresponding carbonyl compound by reacting the alcohol with about 4-6 fold excess of DMAP.HCrO$_3$Cl in a suitable solvent such as, for example, dichloromethane. The particular reaction conditions, i.e. reaction temperature, reaction time and the like, will, of course, vary depending upon the particular alcohol employed. The resulting product contains the desired carbonyl compound and a brown chromium by-product which can be completely removed by filtration with, for example, Celite ® filter aid. Typically, no 4-dimethylaminopyridine is observed in the crude filtrate. Standard recovery techniques may be employed, such as, for example, direct Kugelrohr distillation for sensitive products, or washing with 2 N hydrochloric acid, followed by dilute sodium carbonate wash, drying and distillation or crystallization.

The process of this invention may be illustrated by, but is not intended to be limited to, the following reactions:

| Alcohol | Oxidation of Benzylic Alcohols to Aldehydes Using DMAP.HCrO$_3$Cl | |
|---|---|---|
| | Conditions Equivalents, Time | Product Typical % Yield |
| Ph-CH$_2$OH | DMAP.HCrO$_3$Cl, 3 eq, 3 hrs. | Ph-CHO, 64% |
| 2-thienyl-CH$_2$OH | DMAP.HCrO$_3$Cl, 3 eq, 4 hrs. | 2-thienyl-CHO, 73% |

-continued

Oxidation of Benzylic Alcohols to Aldehydes Using DMAP·HCrO₃Cl

| Alcohol | Conditions Equivalents, Time | Product Typical % Yield |
|---|---|---|
| 2-methylbenzyl alcohol | DMAP·HCrO₃Cl, 4 eq, 15 hrs. | 2-methylbenzaldehyde, 78% |
| 4-methoxybenzyl alcohol | DMAP·HCrO₃Cl, 4 eq, 6 hrs. | 4-methoxybenzaldehyde, 87% |
| piperonyl alcohol (3,4-methylenedioxybenzyl alcohol) | DMAP·HCrO₃Cl, 5 eq, 15 hrs. | piperonal, 98% |
| 4-nitrobenzyl alcohol | DMAP·HCrO₃Cl, 6 eq, 20 hrs. | 4-nitrobenzaldehyde, 43% |
| 3,4-dimethoxybenzyl alcohol | DMAP·HCrO₃Cl, 4 eq, 14 hrs. | 3,4-dimethoxybenzaldehyde, 91% |
| 4-chlorobenzyl alcohol | DMAP·HCrO₃Cl, 5 eq, 21 hrs. | 4-chlorobenzaldehyde, 91% |
| 3,4,5-trimethoxybenzyl alcohol | DMAP·HCrO₃Cl, 3 eq, 14 hrs. | 3,4,5-trimethoxybenzaldehyde, 86% |
| 4-benzyloxybenzyl alcohol | DMAP·HCrO₃Cl, 6 eq, 15 hrs. | 4-benzyloxybenzaldehyde, 88% |

-continued
Oxidation of Benzylic Alcohols to Aldehydes Using DMAP.HCrO₃Cl

| Alcohol | Conditions Equivalents, Time | Product Typical % Yield |
|---|---|---|
| 4-isopropylbenzyl alcohol (CH₃-CH(CH₃)-C₆H₄-CH₂OH) | DMAP.HCrO₃Cl, 4 eq, 14 hrs. | 4-isopropylbenzaldehyde, 72% |
| 4-(3-hydroxypropyl)benzyl alcohol (HOCH₂CH₂CH₂-C₆H₄-CH₂OH) | DMAP.HCrO₃Cl, 4 eq, 2 hrs. | 4-(3-hydroxypropyl)benzaldehyde (HOCH₂CH₂CH₂-C₆H₄-CHO), 62% |

Oxidation of Allylic Alcohols to Aldehydes Using DMAP.HCrO₃Cl

| Alcohol | Conditions, Equivalents, Time | Product, Typical % Yield |
|---|---|---|
| CH₃CH₂CH₂CH=CHCH₂OH | DMAP.HCrO₃Cl, 6 eq, 16 hrs. | CH₃CH₂CH₂CH=CHCHO, 42% |
| C₆H₅-CH=CHCH₂OH | DMAP.HCrO₃Cl, 6 eq, 15 hrs. | C₆H₅-CH=CHCHO, 62% |
| CH₃(CH₂)₅CH=CHCH₂OH | DMAP.HCrO₃Cl, 6 eq, 24 hrs. | CH₃(CH₂)₅CH=CHCHO, 90% |
| CH₃(CH₂)₄CH=C(CH₃)CH₂OH | DMAP.HCrO₃Cl, 6 eq, 12 hrs. | CH₃(CH₂)₄CH=C(CH₃)CHO, 72% |
| (CH₃)₂C=CHCH₂CH₂C(CH₃)=CHCH₂OH | DMAP.HCrO₃Cl, 6 eq, 15 hrs. | (CH₃)₂C=CHCH₂CH₂C(CH₃)=CHCHO, 88% |
| tetrahydropyranyl-O-CH₂CH=CHCH₂OH | DMAP.HCrO₃Cl, 5 eq, 24 hrs. | tetrahydropyranyl-O-CH₂CH=CHCHO, 55% |
| C₆H₅-C(O)OCH₂CH=CHCH₂OH | DMAP.HCrO₃Cl, 4 eq, 24 hrs. | C₆H₅-C(O)OCH₂CH=CHCHO, 75% |

| Oxidation of Allylic Alcohols to Aldehydes Using DMAP.HCrO₃Cl | | |
|---|---|---|
| Alcohol | Conditions, Equivalents, Time | Product, Typical % Yield |
| cyclohex-2-enol (—OH on cyclohexene) | DMAP.HCrO₃Cl, 6 eq, 7 hrs. | cyclohex-2-enone (=O), 74% |
| CH₃-substituted cyclohexene—CH=CH—C(CH₃)=CHCH₂OH (with gem-dimethyl) | DMAP.HCrO₃Cl, 4.5 eq, 2 hrs. | CH₃-substituted cyclohexene—CH=CH—C(CH₃)=CHCHO, 26% |

The following examples further illustrate the invention, and it will be understood that the invention is not limited thereto.

EXAMPLE 1

This example illustrates the preparation of 4-dimethylaminopyridinium chlorochromate.

4-Dimethylaminopyridine (4.00 g, 32.8 mmol) is added to an ice-cold vigorously stirred solution of chromium trioxide (3.27 g, 32.7 mmol) in 20 ml of 1.65 M aqueous hydrochloric acid resulting in a thick yellow-orange slurry. The slurry is stirred in an ice bath for 30 minutes. A yellow-orange solid results which is collected on a sintered glass funnel, washed with two 10 ml portions of ice cold distilled water, kept under suction until moderately dry, and placed under vacuum pump pressure until a dry powder forms. The resulting product is 4-dimethylaminopyridinium chlorochromate, is obtained in a typical yield of about 90–92% of the theoretical yield and is analyzed as follows:

$C_7H_{11}ClCrN_2O_3$. Calc %: C, 32.51; H, 4.28; N, 10.82; Cr, 20.11. Found %: C, 32.70; H, 4.41; N, 10.66; Cr, 20.06.

EXAMPLE 2

This example illustrates the conversion of 3-(4-hydroxymethylphenyl) propanol to its corresponding mono-aldehyde according to the reaction scheme:

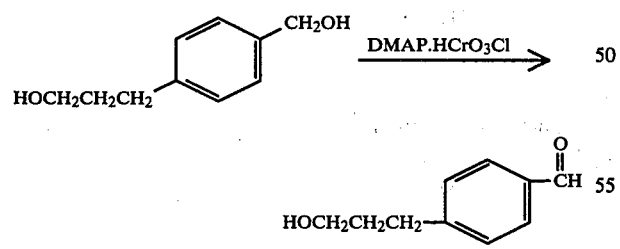

3-(4-hydroxymethylphenyl) propanol (0.250 g, 1.5 mmol) is added in one portion to a stirred suspension of DMAP.HCrO₃Cl (1.55 g, 6.0 mmol) in 25 ml of dichloromethane. The resulting reaction mixture is a yellow-orange suspension. Stirring is continued and the reaction mixture turns brown-black after about 20 minutes. After the reaction has run for about 2 hours, the reaction mixture is diluted with 25 ml of ether and filtered through a 1 cm Celite ® pad. An orange-brown filtrate is recovered, concentrated to an oil and chromatographed on a 33 cm×20 mm column using silica gel. The resulting product is eluted with chloroform to recover any dialdehyde, and the more polar hydroxyaldehyde is eluted with ethyl acetate. The desired hydroxyaldehyde is produced in a typical yield of about 62% whereas the dialdehyde is obtained in a typical yield of only 2%.

The foregoing Example 2 demonstrates the selectivity of the oxidizing agent of this invention in oxidizing benzylic alcohols to benzylic aldehydes rather than simply oxidizing all alcohol groups of the starting compound. By way of contrast, when the oxidizing agent pyridinium chlorochromate is employed under normal conditions (1.5 eq chlorochromate, reaction time 20 minutes) to oxidize the diol of Example 2, a product is obtained which contains both the mono-aldehyde produced in Example 2 and the dialdehyde

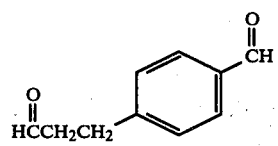

in yield of about 45% and about 32% respectively.

EXAMPLE 3

This example illustrates the conversion of an allylic alcohol to an aldehyde.

Trans-2-hexenol (0.437 g, 4.3 mmol) in 2 ml dichloromethane is added in one portion to a slurry of DMAP.HCrO₃Cl in 20 ml dichloromethane while stirring at room temperature. Stirring is continued for 16 hours during which time dark brown, granular chromium reduction products form. The reaction mixture is then diluted with about 10 ml of petroleum ether. A dark brown precipitate forms which is removed by vacuum filtration through a 1 cm Celite ® pad. The filtrate is recovered and the solvent removed therefrom by distillation via Kugelrohr. The resulting product is trans-2-hexenal which has a boiling point of 50°–52° C./20 mm (compared to the boiling point reported in the literature of 49°–51° C./20 mm), and is obtained in a typical yield of about 42%.

EXAMPLE 4

This example illustrates the oxidation of the compound

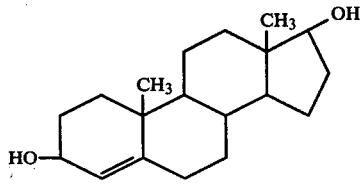
III

Compound III is added to 4 equivalents of DMAP.HCrO₃Cl in dichloromethane and allowed to react for 6 hours resulting in 44% yield of the mono-ketone.

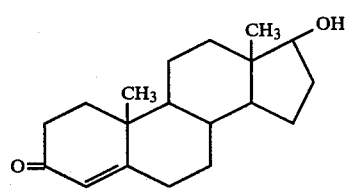
IV while producing only an 11% yield of the diketone

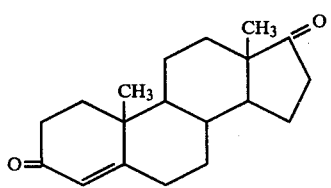
V

By way of contrast, when compound III is oxidized with 1.5 equivalents of pyridinium chlorochromate, approximately equal amounts of IV and V are produced.

EXAMPLE 5

This example illustrates the oxidation of the compound

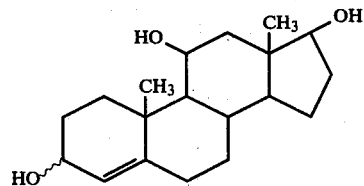
VI

Compound VI (0.183 g, 0.59 mmol) is added in one portion to a suspension of DMAP.HCrO₃Cl (0.53 g, 2.24 mmol) in 25 ml dichloromethane while stirring. The resulting reaction mixture is stirred for 4 hours. Brown chromium reduction products form and are removed by vacuum filtration through a 1 cm Celite ® pad. The filtrate is recovered and rotary-evaporated to yield a brown oil which is chromatographed on 70 g of alumina to yield, as the major component, the following compound:

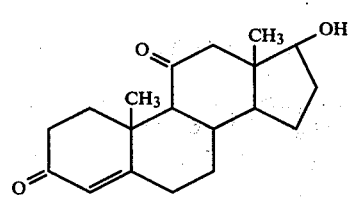
VII in a typical yield of about 49% while producing less than 3% of the triketone

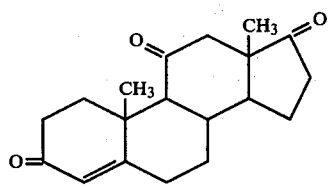
VIII

What I claim and desire to protect by Letters Patent is:

1. 4-dimethylaminopyridinium chlorochromate.

* * * * *